(12) United States Patent
Khoshdel et al.

(10) Patent No.: US 10,588,839 B2
(45) Date of Patent: Mar. 17, 2020

(54) METHOD OF SHAPING HAIR

(71) Applicant: Conopco, Inc., Englewood Cliffs, NJ (US)

(72) Inventors: Ezat Khoshdel, Neston (GB); Prem Kumar Cheyalazhagan Paul, Wirral (GB); Susan Pye, Wirral (GB)

(73) Assignee: CONOPCO, INC., Englewood Cliffs, NJ (US)

(*) Notice: Subject to any disclaimer, the term of this patent is extended or adjusted under 35 U.S.C. 154(b) by 602 days.

(21) Appl. No.: 15/036,459

(22) PCT Filed: Nov. 14, 2014

(86) PCT No.: PCT/EP2014/074677
§ 371 (c)(1),
(2) Date: May 13, 2016

(87) PCT Pub. No.: WO2015/074971
PCT Pub. Date: May 28, 2015

(65) Prior Publication Data
US 2016/0287500 A1    Oct. 6, 2016

(30) Foreign Application Priority Data
Nov. 21, 2013  (EP) ................................ 13193932

(51) Int. Cl.
| | | |
|---|---|---|
| *A61Q 5/04* | (2006.01) | |
| *A61K 8/44* | (2006.01) | |
| *A61K 8/365* | (2006.01) | |
| *A61K 8/33* | (2006.01) | |
| *A45D 2/00* | (2006.01) | |
| *A45D 7/06* | (2006.01) | |
| *A45D 20/04* | (2006.01) | |
| *A61K 8/34* | (2006.01) | |

(52) U.S. Cl.
CPC ............ *A61K 8/44* (2013.01); *A45D 2/001* (2013.01); *A45D 7/06* (2013.01); *A45D 20/04* (2013.01); *A61K 8/33* (2013.01); *A61K 8/345* (2013.01); *A61K 8/365* (2013.01); *A61Q 5/04* (2013.01); *A61K 2800/592* (2013.01); *A61K 2800/805* (2013.01); *A61K 2800/81* (2013.01)

(58) Field of Classification Search
None
See application file for complete search history.

(56) References Cited

U.S. PATENT DOCUMENTS

| | | | |
|---|---|---|---|
| 3,025,218 A | 3/1962 | Strain | |
| 3,470,887 A | 10/1969 | Kremer et al. | |
| 3,482,581 A | 12/1969 | Weigand | |
| 3,805,809 A * | 4/1974 | Zeffren | A61Q 5/04 132/203 |
| 4,192,863 A | 3/1980 | Kondo | |
| 4,349,537 A | 9/1982 | Forbriger, Jr. | |
| 4,409,204 A | 10/1983 | Lang | |
| 4,911,919 A | 3/1990 | Patel | |
| 5,002,761 A | 3/1991 | Mueller | |
| 5,015,470 A | 5/1991 | Gibson | |
| 5,254,336 A | 10/1993 | Hoshowski | |
| 5,635,168 A | 6/1997 | Burns | |
| 5,655,552 A | 12/1997 | Samain | |
| 6,482,808 B1 | 11/2002 | Springob et al. | |
| 6,517,822 B1 | 2/2003 | Buck | |
| 6,723,308 B2 | 4/2004 | Browning | |
| 7,744,859 B2 | 6/2010 | Campain | |
| 7,988,954 B2 | 8/2011 | Chandra | |
| 8,192,730 B2 | 6/2012 | Elliott | |
| 8,324,183 B2 | 12/2012 | Kawano | |
| 2001/0007160 A1 | 7/2001 | Yamaguchi et al. | |
| 2003/0021758 A1* | 1/2003 | Cannell | A61K 8/60 424/70.13 |
| 2003/0108505 A1 | 6/2003 | Cao et al. | |
| 2005/0214238 A1 | 9/2005 | Fukuhara | |
| 2006/0096042 A1 | 5/2006 | Schonert | |
| 2006/0272107 A1* | 12/2006 | Malle | A61K 8/43 8/405 |
| 2007/0298003 A1 | 12/2007 | Chandra | |
| 2008/0019938 A1 | 1/2008 | Elliott | |
| 2008/0019939 A1 | 1/2008 | Verboom | |
| 2009/0126756 A1 | 5/2009 | Syed | |
| 2009/0165812 A1 | 7/2009 | Resnick | |
| 2009/0252697 A1 | 10/2009 | Barbarat | |
| 2009/0320869 A1* | 12/2009 | Fadeeva | A61K 8/60 132/200 |

(Continued)

FOREIGN PATENT DOCUMENTS

| | | |
|---|---|---|
| CN | 1679481 | 10/2005 |
| DE | 2438534 | 2/1976 |

(Continued)

OTHER PUBLICATIONS

Barclay-Nichols, Thickeners: Cationic guar gum, Swift Crafty Monkey Blogspot, 2011, pp. 1-14; http://swiftcraftymonkey.blogspot.com/2011/02/thickeners-cationic-guar-gum.html.
Nature's Aid, "What You Need to Know About Guar Hydroxypropyltrimonium Chloride", 2015, pp. 1-4; http://www.naturesaid.ca/about-guar-hydroxypropyltrimonium-chloride/.
IPRP2 in PCTEP2014074677 dated Dec. 1, 2015, pp. 1 to 9.
IPRP2 in PCTEP2014074998 dated Jan. 15, 2016, pp. 10 to 23.
IPRP2 in PCTEP2014074999 dated Feb. 9, 2016, pp. 24 to 34.
IPRP2 in PCTEP2014075000 dated Jun. 22, 2015, pp. 35 to 47.
Search Report and Written Opinion in EP13193932 dated Feb. 27, 2014, pp. 1 to 6.

(Continued)

*Primary Examiner* — Jyothsna A Venkat
(74) *Attorney, Agent, or Firm* — Foley & Lardner LLP

(57) ABSTRACT

The invention provides a method of shaping hair comprising the following sequential steps: (i) treating the hair by topical application of a hair treatment composition comprising from 2 to 25 wt % of one or more $C_{2-4}$ monoaldehydes, and (ii) mechanically shaping the treated hair.

10 Claims, No Drawings

(56) References Cited

U.S. PATENT DOCUMENTS

| | | | |
|---|---|---|---|
| 2010/0172855 A1 | 7/2010 | Paul | |
| 2010/0196303 A1 | 8/2010 | Paul | |
| 2010/0202994 A1 | 8/2010 | Kasai | |
| 2010/0233114 A1 | 9/2010 | DeGeorge | |
| 2010/0300471 A1* | 12/2010 | Malle | A61K 8/362 132/204 |
| 2010/0307525 A1* | 12/2010 | De Boni | A45D 7/06 132/206 |
| 2011/0052520 A1* | 3/2011 | Nguyen | A61K 8/41 424/70.4 |
| 2011/0256084 A1 | 10/2011 | Dixon | |
| 2012/0093757 A1* | 4/2012 | Murray | A61K 8/042 424/70.22 |
| 2012/0192888 A1 | 8/2012 | Philippe | |
| 2012/0312317 A1 | 12/2012 | Mannozzi | |
| 2015/0128984 A1 | 5/2015 | Paul | |
| 2015/0136167 A1 | 5/2015 | Murray | |
| 2015/0328119 A1 | 11/2015 | Paul | |

FOREIGN PATENT DOCUMENTS

| | | |
|---|---|---|
| DE | 4300320 | 7/1994 |
| EP | 1066019 | 1/2001 |
| EP | 1174111 | 1/2002 |
| EP | 1174112 | 1/2002 |
| EP | 1393708 | 3/2004 |
| EP | 1428497 | 6/2004 |
| EP | 1579843 | 9/2005 |
| EP | 1634570 | 3/2006 |
| EP | 1719545 | 11/2006 |
| FR | 2721823 | 1/1996 |
| FR | 2929508 | 10/2009 |
| JP | 6298629 | 10/1994 |
| JP | 2005272377 | 10/2005 |
| JP | 2005533085 | 11/2005 |
| JP | 2006182702 | 7/2006 |
| JP | 2009519272 | 5/2009 |
| JP | 2010159254 | 7/2010 |
| JP | 2013514264 | 4/2013 |
| WO | WO9405754 | 3/1994 |
| WO | WO03039497 A1 | 5/2003 |
| WO | WO2004004672 | 1/2004 |
| WO | WO2005025524 | 3/2005 |
| WO | WO2005084622 | 9/2005 |
| WO | WO2005084623 | 9/2005 |
| WO | WO2007068400 | 6/2007 |
| WO | WO2008132101 | 11/2008 |
| WO | WO2009003808 | 1/2009 |
| WO | WO2009047251 | 4/2009 |
| WO | WO2009138288 A1 | 11/2009 |
| WO | WO2010001632 | 1/2010 |
| WO | WO2010049434 A2 | 5/2010 |
| WO | WO2010141098 | 12/2010 |
| WO | WO2011074143 | 6/2011 |
| WO | WO2012084532 | 6/2012 |
| WO | WO2012084533 | 6/2012 |
| WO | WO2012122457 | 9/2012 |
| WO | WO2013174575 | 11/2013 |

OTHER PUBLICATIONS

Search Report and Written Opinion in EP13193933 dated Apr. 23, 2014, pp. 7 to 16.
Search Report and Written Opinion in EP13193934 dated Apr. 24, 2014, pp. 17 to 23.
Search Report and Written Opinion in EP13193935 dated Apr. 23, 2014, pp. 24 to 29.
Search Report and Written Opinion in PCTEP2013057809 dated Jul. 17, 2013, pp. 1 to 12.
Search Report and Written Opinion in PCTEP2014074677 dated Jan. 21, 2015, pp. 13 to 21.
Search Report and Written Opinion in PCTEP2014074999 dated Feb. 26, 2015, pp. 22 to 38.
Search Report and Written Opinion in PCTEP2014075000 dated Jun. 22, 2015, pp. 39 to 50.
Search Report and Written Opinions in PCTEP2014074998 dated Jun. 19, 2015, pp. 51 to 69.
Co-pending Application: Applicant: Murray et al., U.S. Appl. No. 14/400,965, filed Nov. 13, 2014.
Opposition notice in EP137157085; dated Jan. 14, 2019.

\* cited by examiner

METHOD OF SHAPING HAIR

FIELD OF THE INVENTION

This invention relates to a method of shaping hair, and more particularly a method of shaping hair without breaking the hair disulfide bonds.

BACKGROUND AND PRIOR ART

Many people with naturally kinky, curly, or even wavy hair often desire to straighten their hair. Permanent hair straightening compositions that are on the market are based on chemical treatment of the hair in a two-step process using reducing agents to break hair disulfide bonds, followed by a neutralisation or oxidation step to re-establish new disulfide bonds in the desired configuration. Such systems have various negatives associated with them; in that the process itself is difficult to conduct, in many instances this straightening process is undertaken by a qualified hairdresser in a professional salon. Furthermore the straightening process damages the hair, has an unpleasant odour and can cause irritation to the scalp.

Surprisingly we have found that hair can be shaped without causing the chemical damage which is traditionally associated with permanent hair straightening processes involving breakage of the hair disulfide bonds. Advantageously the method of the invention does not necessarily require the use of high temperature heated implements such as straightening irons and can be accomplished by a consumer without intervention of a professional hairdresser. Furthermore, hair shaped with the method of the invention remains shaped even after subsequent washing.

SUMMARY OF THE INVENTION

The present invention provides a method of shaping hair comprising the following sequential steps:
(i) treating the hair by topical application of a hair treatment composition comprising from 2 to 25 wt % of one or more $C_{2-4}$ monoaldehydes, and mechanically shaping the treated hair.

DETAILED DESCRIPTION AND PREFERRED EMBODIMENTS

Suitable $C_{2-4}$ monoaldehydes for use in the invention include aliphatic monoaldehydes of the general formula:

in which n is an integer of from 1 to 3;
X is —H or —OH, and
each Y is independently selected from —H and —OH.

Preferred $C_{2-4}$ monoaldehydes of the above general formula include at least one —OH group and more preferably two —OH groups.

A particularly preferred $C_{2-4}$ monoaldehyde for use in the invention is glyceraldehyde.

The one or more $C_{2-4}$ monoaldehydes as described above may be used as the sole hair shaping active in the formulated hair treatment composition. In such a case, the total level of $C_{2-4}$ monoaldehyde preferably ranges from 2 to 20 wt % and more preferably from 2 to 15 wt %, by weight based on the total weight of the hair treatment composition.

For example, glyceraldehyde may be used as the sole hair shaping active in the formulated hair treatment composition, at a level which preferably ranges from 2 to 20 wt % and more preferably from 2 to 15 wt %, by weight based on the total weight of the hair treatment composition.

Alternatively, the one or more $C_{2-4}$ monoaldehydes as described above may be combined with additional hair shaping actives in the formulated hair treatment composition.

Examples of such additional hair shaping actives which may be used in this context include aliphatic carboxylic acids having a molecular weight ($M_W$) ranging from 60 to 300 g/mol, and a $pK_a$ (measured at 25° C. in water) ranging from 2 to 8.5.

Preferably the aliphatic carboxylic acid has a $pK_a$ (measured at 25° C. in water) ranging from 2 to 4.5, more preferably from 2.1 to 4.2.

Aliphatic monocarboxylic acids which may be used as additional hair shaping actives in the method of the invention have a structure corresponding to the following general formula (I):

$R^1$ is a monovalent saccharide residue or a monovalent saturated alkyl radical of formula $R^3$—(A)—;
$R^3$ is a monovalent radical selected from H—, $HOCH_2$— and saturated linear alkyl radicals of formula $X(CH_2)_n$—;
X is a monovalent radical selected from H—, HO—, $H_2N$—, $H_2NC(O)$—, $(HOCH_2)_3C$—NH—, $(HOCH_2CH_2)_2N$— and $H_3CC(O)$—;
n is an integer ranging from 1 to 8;
A is a divalent radical selected from —C(O)— and —C($R^4$)($R^5$)—;
$R^4$ is a monovalent radical selected from —H, —OH, —$CH_2OH$ and —$NH_2$, and
$R^5$ is a monovalent radical selected from —H, —$CH_2OH$, —$CH_3$ and —$CH_2CH_3$.

Preferably $R^1$ in general formula (I) above is a monovalent monosaccharide residue (such as a glucose or galactose residue), or a monovalent saturated linear alkyl radical of formula $R^3$—(A)—;
in which $R^3$ is selected from H—, $HOCH_2$— and $H_3C$—;
and A is a divalent radical selected from —C(O)—, —CH(OH)—, —C($CH_3$) ($CH_2OH$)— and —C($CH_2CH_3$)($CH_2OH$)—.

Specific examples of such monocarboxylic acids include lactic acid, glyoxylic acid, glycolic acid, glucuronic acid, 2,2-bis(hydroxymethyl)propionic acid, lysine, 2-hydroxyoctanoic acid, acetic acid, glycine, serine, succinamic acid, levulinic acid, galacturonic acid, tricine, bicine and 2,2-bis(hydroxymethyl)butyric acid.

Aliphatic dicarboxylic acids which may be used as additional hair shaping actives in the method of the invention have a structure corresponding to the following general formula (II):

in which $R^1$ is a divalent, saturated or unsaturated, linear or branched hydrocarbyl radical having from 1 to 4 carbon atoms, and which may optionally be substituted with one or more hydroxyl groups.

Preferably $R^1$ in general formula (II) above is a divalent saturated linear alkyl radical of formula —$[CH(X)]_n$— in which n is an integer ranging from 1 to 3 and each X is independently selected from —H and —OH.

Specific examples of such dicarboxylic acids include malonic acid and tartaric acid.

Aliphatic tricarboxylic acids which may be used as additional hair shaping actives in the method of the invention have a structure corresponding to the following general formula (III):

$$HOOC-CH_2-R^1-COOH \quad (III)$$

in which $R^1$ is a divalent, saturated or unsaturated, linear or branched hydrocarbyl radical having from 1 to 3 carbon atoms, which is substituted with one —COOH group and which may optionally be substituted with one or more hydroxyl groups.

Preferably $R^1$ in general formula (III) above is selected from —C(COOH)═C(H)— and —C(X)(COOH)—CH$_2$— radicals in which X is selected from —H and —OH.

Specific examples of such tricarboxylic acids include citric acid, aconitic acid and tricarballylic acid.

When the one or more $C_{2-4}$ monoaldehydes as described above are combined with additional hair shaping actives in the formulated hair treatment composition, the level of these materials preferably ranges from 3 to 20 wt % and more preferably from 4 to 15 wt %, by total weight $C_{2-4}$ monoaldehydes and additional hair shaping actives based on the total weight of the hair treatment composition.

Particularly good results have been observed with mixtures of glyceraldehyde and citric acid. The weight ratio of the aldehyde to the acid in such a mixture preferably ranges from 5:1 to 1:2, more preferably from 3:1 to 2:3, and is most preferably from about 1:1.

Particularly good results have also been observed with mixtures of glyceraldehyde and lysine. The weight ratio of the glyceraldehyde to the lysine in such a mixture preferably ranges from 5:1 to 1:2, more preferably from 3:1 to 1:1, and is most preferably about 2:1. The inventors have observed that such mixtures of glyceraldehyde and lysine provide straightness benefits both with and without the use of hot tools (as are further described below).

Preferred hair treatment compositions for use in the invention have a conditioning gel phase, which may be generally characterized as a gel (Lβ) surfactant mesophase consisting of surfactant bilayers. Such a conditioning gel phase may be formed from a cationic surfactant, a high melting point fatty compound and an aqueous carrier. Typically these components are heated to form a mixture, which is cooled under shear to room temperature. The mixture undergoes a number of phase transitions during cooling, normally resulting in a gel ($L_\beta$) surfactant mesophase consisting of surfactant bilayers.

Examples of suitable cationic surfactants which are useful for forming the conditioning gel phase include quaternary ammonium cationic surfactants corresponding to the following general formula:

$$[N(R^1)(R^2)(R^3)(R^4)]^+ \quad (X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the hair treatment composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty compound can be used as a single compound or as a blend or mixture of at least two high melting point fatty compounds. When a blend or mixture of fatty compounds is used, the melting point means the melting point of the blend or mixture.

Suitable fatty compounds of this type have the general formula R—X, wherein R is an aliphatic carbon chain and X is a functional group (e.g. alcohol or carboxylic acid or a derivative thereof such as ester or amide).

R is preferably a saturated aliphatic carbon chain comprising from 8 to 30 carbon atoms, preferably from 14 to 30 carbon atoms, more preferably from 16 to 22 carbon atoms.

R can contain, in addition to carbon and hydrogen atoms, ether linkages, and other groups such as amino groups. Preferably R is a linear alkyl chain comprising from 8 to 30 carbon atoms, preferably from 14 to 30 carbon atoms, more preferably from 16 to 22 carbon atoms.

X is preferably an —OH group.

Most preferably, the fatty compound is a fatty alcohol of general formula $CH_3(CH_2)_n$OH, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty compounds may also be suitable.

The level of fatty compound suitably ranges from 0.01 to 10 wt %, preferably from 0.1 to 8 wt %, more preferably from 0.2 to 7 wt % and most preferably from 0.3 to 6 wt % (by weight based on the total weight of the hair treatment composition).

The weight ratio of cationic surfactant to fatty compound is suitably from 1:1 to 1:10, preferably from 1:1.5 to 1:8, optimally from 1:2 to 1:5.

Advantageously, the method of the invention does not require the breakage of hair disulfide bonds, and hair treatment compositions for use in the invention do not require the incorporation of reducing agents. It is preferred that such materials, if included at all, are present in minor quantities only.

The term "reducing agent" in the context of this invention means an agent which is effective to break hair disulfide bonds when applied to hair for a period ranging from about 3 to 15 minutes and at a temperature ranging from about 20 to 30° C. Examples of such reducing agents are ammonium thioglycolate (in a solution having a pH of between about 7 and 10.5), glyceryl monothioglycolate (employed at a pH of less than 7), thioglycolic acid, dithioglycolic acid, mercaptoethyl amine, mercaptopropionic acid, dithioglycolate and alkali metal or ammonium sulfites or bisulfites.

A hair treatment composition for use in the method of the invention will preferably include from 0 to 0.1 wt %, more preferably from 0 to 0.01 wt %, and most preferably from 0 to 0.001 wt % reducing agents as defined above (by weight based on the total weight of the hair treatment composition).

Hair treatment compositions for use in the invention will generally comprise at least 60 wt %, preferably at least 70 wt % and more preferably at least 80 wt % water (by weight based on the total weight of the hair treatment composition). Preferably, the hair treatment composition comprises no more than 95 wt % and more preferably no more than 90 wt % water (by weight based on the total weight of the hair treatment composition).

Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The hair treatment composition may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

Preferably, the hair treatment composition is a single dose composition. The term "single dose" in the context of this invention means that the hair treatment composition is to be applied to the hair in one go.

Preferably, the hair treatment composition is applied to the hair in the form of a 100 to 300 ml single dose, more preferably a 150 to 250 ml single dose.

Preferably, the hair treatment composition is applied to the hair at a temperature from 15 to 40° C., and more preferably at a temperature from 20 to 30° C.

Preferably, the hair treatment composition is applied to dry hair. The term "dry hair" in the context of this invention generally means hair from which free water (i.e. water disposed as a film or droplets on the cuticle surface) has been substantially removed. Hair may be dried by exposure to air, by use of a heated hair drying appliance, by rubbing with a water-absorbent article, or by a combination of any of these methods. Preferably, the dry hair will not have been washed or actively wetted, (such as by shampooing, conditioning, rinsing or otherwise treating with an aqueous composition) in the preceding 2 hours and more preferably in the preceding 3 hours prior to topical application of the hair treatment composition in accordance with step (i) of the method of the invention, and will have been permitted to acclimatise to atmospheric conditions. In such circumstances there is substantially no free water present which interferes with the adsorption of the hair treatment composition on application. A suitable indicator of dry hair in the context of this invention would be a hair fibre whose calculated water content does not exceed 25 wt % by weight based on the total weight of the hair fibre.

Preferably, the hair treatment composition is worked through the hair after topical application.

Preferably, after working through the hair, the hair treatment composition is then left to penetrate the hair for a period of at least 5 up to about 90 minutes, more preferably for at least 10 up to about to 60 minutes and most preferably for at least 15 up to about 40 minutes.

The hair treated in accordance with step (i) of the method of the invention is preferably dried prior the commencement of step (ii). The hair may be dried by exposure to air, by use of a heated hair drying appliance, by rubbing with a water-absorbent article, or by a combination of any of these methods.

Preferably in step (ii) of the method of the invention, the hair is mechanically straightened. For example, the hair may be pulled, combed, smoothed, pressed or flattened into a straightened configuration.

A hot tool, such as an electrically heated flat hair iron or hand-held hair dryer, may be used in the mechanical shaping step. Such tools apply high levels of heat directly to the hair. Most operate in the 45° C. to 250° C. range, and are usually employed at temperature settings ranging from 50° C. to about 220° C., depending on the particular tool.

Particularly good results have been obtained when the hair is mechanically straightened in step (ii) of the method of the invention with a hot tool such as an electrically heated flat hair iron. In such a case, it is preferred that the operating temperature of the hot tool ranges from 120 to 220° C., more preferably from 150 to 220° C., and most preferably from 170 to 220° C.

However, hair shaping benefits are also observed without the use of hot tools such as those described above. For example, in step (ii) of the method of the invention the hair may instead be mechanically straightened by combing it into a straightened configuration at a temperature from 20 to 30° C.

Advantageously, the invention also provides a method for re-shaping hair in which hair which has been treated and shaped in accordance with steps (i) and (ii) as described above is rinsed, and mechanically re-shaped before and/or after drying.

Hair to be mechanically re-shaped as described above may be rinsed with water alone or with shampoo. Preferably in the mechanical reshaping step the hair is mechanically re-straightened by combing it into a straightened configuration at a temperature from 20 to 30° C.

One or more (e.g. two or three) cycles of rinsing, mechanical re-shaping and drying as described above may be carried out.

The present inventors have surprisingly found that hair may be durably shaped by the method of the invention. The term "durably shaped" in the context of this invention means that the hair shape persists after washing. Preferably more than 50% of the hair shape persists after 3 washes.

The invention is further illustrated with reference to the following, non-limiting Examples.

EXAMPLES

All ingredients are expressed by weight percent of the total formulation, and as level of active ingredient.

Example 1

Dark brown wavy #6 European hair switches were soaked for 30 minutes in solutions of 2% glyceraldehyde at its natural or spontaneous pH.

All switches were combed straight and were dried in drying cabinets. When dry the switches were ironed with 7 passes using straighteners at 200° C.

The switches were subsequently washed after 3 days with base shampoo and combed straight and dried in drying cabinets.

When dry the switches were combed and pictures taken. The volumes of the switches were measured using an image analysis kit. The results are given in Table 1.

TABLE 1

Volumes of treated hair switches in mm$^2$ after a single heat treatment and subsequent washing. There was a 3 day gap between washings.

|  | after ironing + 1 wash | % benefit after ironing + 1 wash | after ironing + 2 washes | % benefit after ironing + 2 washes |
|---|---|---|---|---|
| Control | 14839.14 | 0 | 12611.16 | 0 |
| Glyceraldehyde | 10927.15 | 26.4 | 11191.17 | 11.3 |

If the switches are visually straight then the volume of the switches (actually the projection of the volume in mm$^2$ on to an image plane) is a measure of the straightness benefits of the treatment.

The results show that the glyceraldehyde with heat treatment provides durable straightness benefits.

Example 2

Dark brown wavy #6 European hair switches were soaked for 30 minutes in solutions of 2% citric acid/2% glyceraldehyde and 3% citric acid/3% glyceraldehydes respectively. Control switches were soaked in water.

All switches were combed straight and were dried in drying cabinets.

When dry the switches were ironed with 7 passes using straighteners at 200° C. They were subsequently washed with base shampoo and combed straight and dried in drying cabinets.

When dry the switches were combed and pictures taken. The volumes of the switches were measured using an image analysis kit. These are given in Table 2. Two experiments on two different days were performed.

TABLE 2

Volumes of treated hair switches in mm$^2$ with different levels of citric acid and glyceraldehyde with water as control after heat treatment and subsequent wash after 3 days.

| Treatment | Control volume | Treatment volume | % benefit over control |
|---|---|---|---|
| 2% glyceraldehyde + 2% citric acid | 16923 | 9189 | 45.7 |
| 3% glyceraldehyde + 3% citric acid | 16077 | 9261 | 42.4 |

If the switches are visually straight then the volume of the switches (actually the projection of the volume in mm$^2$ on to an image plane) is a measure of the straightness benefits of the leave-on treatment.

The results show that the combination of citric acid and glyceraldehyde shows excellent straightness benefits even after 1 wash.

Example 3

Dark brown wavy #6 European hair switches were soaked for 30 minutes in solutions of single materials and combinations of materials. Control switches were soaked in water.

All switches were combed straight and were dried in drying cabinets. When dry the switches were combed straight and pictures taken. The volumes of the switches were measured using an image analysis kit. These are given in Table 3.

TABLE 3

Volumes of treated hair switches with water as control and no heat treatment

| Treatment | volume | % benefit |
|---|---|---|
| Water (control) | 15889 | 0 |
| 4% Glyceraldehyde | 12458 | 21.6 |
| 2% Lysine | 9975 | 37.2 |
| 4% Glyceraldehyde + 2% Lysine | 6019 | 62.1 |

If the switches are visually straight then the volume of the switches (actually the projection of the volume in mm$^2$ onto an image plane) is a measure of the straightness benefits of the leave-on treatment.

The results show that the combination of lysine and glyceraldehyde provide a synergistic benefit.

The invention claimed is:

1. A method of straightening hair comprising the following sequential steps:
   (i) treating the hair by topical application of a hair treatment composition comprising:
       a mixture of glyceraldehyde; and
       an additional hair straightening active selected from citric acid or lysine; and
   (ii) mechanically straightening the treated hair with a hot tool with an operating temperature ranging from 120 to 220° C., or by combing it into a straightened configuration at a temperature from 20 to 30° C.;
   wherein:
       the combined level of glyceraldehyde and citric acid or lysine ranges from 4 to 15 wt %, based on the total weight of the hair treatment composition;
       the weight ratio of the glyceraldehyde to the citric acid or lysine in the mixture ranges from 3:1 to 2:3; and wherein the method does not break hair disulfide bonds; the hair treatment composition does not include reducing agents.

2. The method according to claim 1, wherein the method further comprises rinsing the treated hair and mechanically re-straightening the hair.

3. The method according to claim 2, wherein the hair is mechanically re-straightened at a temperature from 20 to 30° C.

4. The method according to claim 1, wherein the hair treatment composition further comprises a conditioning gel phase comprising a cationic surfactant, a high melting point fatty compound, and an aqueous carrier.

5. The method according to claim 1, wherein the weight ratio of the glyceraldehyde to the citric acid or lysine is 1:1.

6. A method of straightening hair comprising the following sequential steps:
(i) treating the hair by topical application of a hair treatment composition comprising:
a mixture of glyceraldehyde; and
an additional hair straightening active selected from citric acid or lysine; and
(ii) mechanically straightening the treated hair at a temperature from 20 to 30° C.;
wherein:
the combined level of glyceraldehyde and citric acid or lysine ranges from 4 to 15 wt %, based on the total weight of the hair treatment composition; and
the weight ratio of the glyceraldehyde to the citric acid or lysine in the mixture ranges from 5:1 to 1:2 wherein the method does not break hair disulfide bonds and wherein the hair treatment composition does not include reducing agents.

7. The method according to claim 6, wherein the method further comprises rinsing the treated hair and mechanically re-straightening the hair.

8. The method according to claim 7, wherein the hair is mechanically re-straightened at a temperature from 20 to 30° C.

9. The method according to claim 6, wherein the weight ratio of the glyceraldehyde to the citric acid or lysine in the mixture ranges from 3:1 to 2:3.

10. The method according to claim 6, wherein the hair treatment composition further comprises a conditioning gel phase comprising a cationic surfactant, a high melting point fatty compound, and an aqueous carrier.

* * * * *